(12) United States Patent
Vasileiadis et al.

(10) Patent No.: US 6,963,018 B2
(45) Date of Patent: Nov. 8, 2005

(54) INTEGRATED PROCESSES FOR OLEFIN AND POLYOLEFIN PRODUCTION

(76) Inventors: Savvas Vasileiadis, 15549 Dearborn St., North Hills, CA (US) 91343; Zoe Ziaka-Vasileiadou, 15549 Dearborn St., North Hills, CA (US) 91343

( * ) Notice: Subject to any disclaimer, the term of this patent is extended or adjusted under 35 U.S.C. 154(b) by 364 days.

(21) Appl. No.: 09/973,459

(22) Filed: Oct. 10, 2001

(65) Prior Publication Data

US 2002/0099248 A1 Jul. 25, 2002

Related U.S. Application Data

(60) Provisional application No. 60/237,202, filed on Oct. 3, 2000.

(51) Int. Cl.[7] ............................ C07C 2/04; C07C 5/32; C07C 5/333
(52) U.S. Cl. ................... 585/654; 585/510; 585/518; 585/519; 585/659; 585/660; 585/661; 585/655
(58) Field of Search ................. 585/654, 655, 585/659, 660, 661, 510, 518, 519, 616, 629, 330, 379

(56) References Cited

U.S. PATENT DOCUMENTS 5,202,517 A * 4/1993 Minet et al. ................. 585/655

OTHER PUBLICATIONS

Vasileiadis, S., Ziaka, Z., "New integrated process for olefin and polyolefin production", paper #14, in Novel Reactors and Processes, 37th SSCRE meeting, Hong Kong, China, Aug. 2002.*

* cited by examiner

Primary Examiner—Walter D. Griffin
Assistant Examiner—Tam M. Nguyen

(57) ABSTRACT

Novel processes for the production of polyolefins, other polymers, and oxygenated compounds, such as polypropylene, polyethylene, polybutene-1, poly(isobutylene), polystyrene, poly(1,3-butadiene), ethylene oxide, propylene oxide, acrylonitrile, acrolein and others, within gas phase and slurry phase type reactors, from olefins produced via the catalytic dehydrogenation of corresponding paraffins and other monomers inside permeable catalytic membrane reactors or non-permeable conventional reactors. The developed processes can produce both homopolymers and copolymers depending on the operating conditions of the preceding dehydrogenation permreactor. The invented processes utilize integrated separation, recycling and re-reaction operations of the unconverted olefins, paraffins and other utilized monomers and hydrocarbon molecules. Product hydrogen from the dehydrogenation reactions can be fed directly into the polymerization reactors as a chain transfer agent to adjust the molecular weight and structure of the produced polyolefins and other polymers. Moreover, integrated olefin-parffin membrane separators and fluid bed polymerization reactors for conversion of olefins to polyolefins are invented Also, integrated dehydrogenation permreactors (membrane based reactors) and fluid bed polymerization reactors are invented which finally produce polyolefins from paraffin feed within a single module. These last integrated reactors can be also used for production of other final polymers through combined dehydrogenation-polymerization, such as polystyrene and poly(1,3-butadiene).

20 Claims, 6 Drawing Sheets

INTEGRATED PROCESSES FOR OLEFIN AND POLYOLEFIN PRODUCTION

This application claims the benefit of provisional application Ser. No. 60/237,202 filed Oct. 3, 2000.

TECHNICAL FIELD

This invention relates to new processes for production of polyolefins and other polymers in gas phase and slurry phase reactors via coordination type polymerization, from olefins and monomers produced through the catalytic dehydrogenation of corresponding paraffins and other hydrocarbon molecules in permeable reactors (so called permreactors or membrane reactors) The invented processes utilize also membrane type permeators in the downstream of the polymerization reactor for separation of the unconverted olefins from the paraffin, hydrocarbon diluents and recycling of each of those chemicals to the corresponding process. The integrated use of product hydrogen from the dehydrogenation reactors into the polymerization reactors as a chain transfer agent to adjust the molecular weight and structure of the produced polymers is an additional feature of the invention. Further, the produced dehydrogenated olefins can be also used in downstream oxidation or synthesis type reactions and reactors for production of specialty chemicals. Moreover, another part of the invention relates to integrated olefin-paraffin membrane separators and fluid bed polymerization reactors within the same module, which are used for production of polyolefins from the permeated (separated) olefin monomers. Another part of the invention relates to integrated dehydrogenation permreactors and fluid bed polymerization reactors which produce polyolefins and other polymers from paraffins and other feed hydrocarbons within a single integrated dehydrogenation-polymerization module.

BACKGROUND OF THE IVENTION

This invention relates to processes which convert paraffins into olefins via dehydrogenation steps and the produced olefins into polyolefins via polymerization steps. The processes are more effective than existing processes and equipment because they integrate more than one process operations into a single process or vessel and utilize recycling of unreacted reactants and products to increase product yield and overall process efficacy and economy. The todays demand for polyolefins, especially polyethylene and polypropylene is high and more effective production methods are in need in terms of reduction in capital and operating expenses. Beyond polyolefins the invention can be applied to production of other polymers from monomers coming out of dehydrogenation reactions. Moreover, the dehydrogenated olefins can be also used in downstream oxidation or synthesis type reactions and reactors for production of specialty chemicals.

Specifically, production of most isotactic, linear polyolefins from $C_2$–$C_5$ monomers such as polypropylene (PP), high density and low density polyethylene (PE), polybutene-1, poly-4-methylpentene-1, take place with coordination polymerization Also other type of polymers such as polystyrene and polydienes (i.e., poly(1,3-butadiene)) are made by using coordination catalysts and are discussed below as well. Both stirred bed (slurry-liquid phase type) reactors and fluid bed (gas phase using solid supported catalysts) reactors can be employed in coordination polymerization as shown below. Stirred bed reactors to be used can be of a horizontal or vertical vessel type and involve a colloidal catalytic dispersion or a soluble type catalyst, which usually is a coordinated complex (i.e., Ziegler-Natta type catalyst) formed by an organometallic compound (e.g., aluminum alkyl such as dichloroethyl aluminum) with a transition metal salt (e.g., titanium tetrachloride, titanium trichioride) in a hydrocarbon solvent (e.g., hexane, heptane). The so-called Ziegler process for production of high density PE, PP and copolymers of PP-PE (polypropylene-polyethylene) is such process implementation. A modified process (i.e., Philips) requires the use of supported metal oxide catalysts in a similar type of multiphase stirred bed system. Supported catalysts that can be used include chromium, zinc, molybdenum, tin, cobalt, nickel metals on alumina, silica, titania or related supports. Such type of commercially established processes and modifications of these operate at reaction conditions which range from T=50–200° C. and P=1–30 atm.

Gaseous type fluid bed reactors can also carry the coordination polymerization reaction for production of similar structure and density propylene, ethylene, butylene and higher polymers and copolymers. The fluid bed uses only a suspension of catalytic powder of the same metal supported composition and structure as described above in the solution type polymerization processes. Such fluid bed reactor processes operates at moderate pressures (20–30 atm) and temperatures (50–200° C.) and recovers polymer in the form of solid particles under high yields per unit mass of catalyst Since polymerization processes are exothermic the heat of reaction is removed by cooling the reactor externally or internally (by vaporizing a suitable diluent) or by circulating the unreacted gas through external cooling devices.

Experimental results from catalytic permreactors (membrane reactors) for paraffin (e.g., propane, ethane, butane) dehydrogenation reactions have been reported in earlier literature communications. Current implementation of catalytic permreactors and perneators with various permselective wall materials has been also demonstrated in other hydrocarbon processing and upgrading reactions such as in steam and $CO_2$ reforming of metane and natural gas.

SUMMARY OF THE INVENTION

The invention described herein pertains to the use and operation of multifunctional permeable paraffin dehydrogenation reactors and derivedelated integrated paraffin dehydrogenation, olefin polymerization, olefin-paraffin separation and recycling systems for production of polymer grade olefins through catalytic dehydrogenation reactions of paraffin feedstocks. Other integrated dehydrogenation-polymerization reactions can be applied with the process. Moreover, the dehydrogenated olefins can be also used in downstream oxidation or synthesis type reactions and reactors for production of specialty chemicals such as ethylene oxide and ethylene glycol, acetaldehyde, acrolein and acrylic acid, acrylonitrile. In addition, the invention relates to a process using integrated olefin-paraffin separators and fluid bed polymerization reactors which produce polyolefins from olefinm/pa mixtures within a single module. In addition, the invention relates to a process using integrated dehydrogenation pernreactors and fluid bed polymerization reactors which produce polyolefins and other polymers from paraffins and other hydrocarbons within a single module. Polymers such as polyethylene, polypropylene, polybutene-1, poly(isobutylene) and with higher monomer units can be produced.

Production of polymer grade olefins through polymeization reactions usually requires pure monomers as feedstocks to avoid catalyst and solvent contamination and rapid loss of catalyst activity in the polymerization vessel. Depending on the type of the utilized polymerization reactor, polymerization process (e.g., bulk, solution, suspension, emulsion, gas phase) and the type of chain propagation reactions (i.e., stepreaction, radical chain (addition), ionic, coordination) the purity, flowrate and concentration of the olefinic monomers may vary in the reactor feed. These monomer variables are coupled with the polymerization temperature, pressure and the volume of the reactor to make for the production of specific polymers within the desired range of molecular weight, structure and properties (i.e., crystallinity, transparency, viscosity, tensile and impact strength and others).

The above described coordination polymerization processes can utilize hydrogen within the reactor as a chain transfer agent to reduce molecular weight and possibly to achieve branching which contributes to a decreased crystallinity product wherein such product is required. Moreover, the monomer olefin can be diluted with a paraffin or cycloparaffin during the polymerization reaction in both type of polymerization peoeesses mentioned above. In our invented processes described below, we seek to utilize as part of the diluent or solvent in the polymerization the unreacted paraffin (i.e., propane for polypropylene production, butene for polybutene-1 production) to increase the process efficacy and economy.

It is important for the invented olefin production processes (i.e, paraffin dehydrogenation reactor) to deliver purified olefins as monomer or mixtures of purified olefins with hydrogen (monomer plus a chain tnansfer agent) to the above described polymerization processes. Unreacted paraffins such as ethane, propane, butane, and other reactant hydrocarbons respectively and possibly inert gases such as argon or nitrogen (which usually are used as sweep gases in the preceding dehydrogenation permreactors to increase paraffin conversion) can he fed as diluents into the polymerization reactor together with the olefinic monomers. Unreacted paraffins such as ethane, propane and butane can act as solvents in slurry-solution type and fluid bed type polymerization vessels in the liquid, vapor or gas phase. They can be also mixed in the polymerization reactor with a higher paraffin (especially in the slurry-solution type of vessels) such as isopentane, hexane, heptane in order to increase the solvent efficiency towards the formed polymer. Moreover, as aforementioned, the unreacted paraffins can be used as diluents to decrease the monomer or polymer concentration in both type of polymerization processes; they can also promote phase mixing during polymerization and remove exothermic beat of polymerization by vaporization at the reaction conditions. These low molecular weight olefins and corresponding paraffins have low boiling points and under usual polymerization conditions (P=25–35 atm, T=55–70° C.) they can be transferred from the liquid to the gas phase through boiling. By utilizing the unreacted paraffins in polymerization, the proposed processes seek to eliminate extensive paraffinlolefin separation. costs before the polymerization process. However, the unutilized paraffin from the polymerization reactor has to be recycled into the dehydrogenator for continuous reaction and production of olefins as shown in FIGS. 1&2 below. The solvent/diluent type paraffin has to be separated from the unreacted olefin monomers which are also exiting from the polymerization reactor. The proposed separation as shown in the Figures can be done by the use of polymer or composite reactive membranes of dense or nanoporous structure, containing Cu, Ag, Zn, Cr, Mn, Fe typemetal ions which have an affinity to form a transporting complex with the permeating olefin (e.g., propylene, ethylene, butylene). Moreover, a facilitated type permeation of olefins via liquid membranes, or via ion exchange membranes can be also used as a suitable process for the proposed olefin-paraffin separation. The membrane type separation processes are in direct competition with the currently applied in industry low temperature distillation which is demanding energetically and economically. Thus, the membrane processes seek to reduce capital and operational costs, while the overall invented process seeks to get rid of the necessity step of separating olefin from paraffin before the polymerization.

Key variables for the consecutive polymerization reactor are the molar flowrate (throughput), composition and concentration of the olefinic monomer stream exiting from the dehydrogenation reactor. These parameters together with the reaction conditions and volume of the polymerization reactor define the monomer (propylene) concentration which in turn affects the molecular weight of the formed polymer. Use of permreactors (membrane reactors) as dehydrogenators provides beneficial increases in paraffin conversion and olefin yield per reactant (e.g., propane, ethane, butane) pass, therefore contributing to increases in polypropylene, polyethylene, polybutene-1 yields in the consecutive polymerization reactor. Another benefit by using the dehydrogenation permreactor is supply of regulated mixtures of olefin and hydrogen for polymerization which make for both the monomer and chain transfer agent for controlling the polymer molecular weight. In addition, where necessary, supply of regulated mixtures of olefin, hydrogen and unreacted paraffin (as diluent or solvent) is also possible by adjusting the. reaction conditions in the dehydrogenator. As an example an increase in dehydrogenation pressure or a decrease in temperature will increase the amount of unreacted paraffin (diluent or solvent) in the exit of the reactor.

Increases in paraffin conversion and olefin yield at the catalytic permreactor exit are due to the enhancement of the reaction rate of the paraffin dehydrogenation reaction caused by the permeation of mainly hydrogen and in a lesser degree of the olefin (e.g., ethylene, propylene, butene-1) through the walls of an inorganic, metal or composite (inorganic-metal) permreactor. A catalytically modified inorganic or composite membrane can be also used in the permreactor to increase both the membrane selectivity to hydrogen and olefin and also the rate of the dehydrogenation reaction due to its catalytic nature. Olefin yield increases by the use of the pernreactors are translated into a richer olefin feed than the one obtained by the use-operation of the conventional plug flow (fixed bed) reactor. This effect in turn results to higher polymer (polyolefin) yields in the adjacent polymerzzation reactor. Both stirred (solution) bed and fluid bed coordination type polymerization reactors can be used to convert the exit olefin mixture into polyolefins.

The configuration, embodiment shown in FIG. 1 is suitable for production of polyolefins (e.g., polyethylene, polypropylene, polybutene-1, poly(isobutylene), poly(4-methylpentene-1 and other polymers) with moderate to low polymer molecular weight due to the strong presence of hydrogen as a chain tnnnsfer agent in the mixture fed into the polymerization reactor.

The combined mixture of parnafiolefin-hydrogen is fed into the polymerization reactor D. Paraffin can be a diluent or solvent in the coordination type polymerization (slurry or gas phase reaction) and is recycled from the outlet of the polyolefin reactor D into the initial permreactor A for continuous dehydrogenation reaction after the separation in permeator (separator) E. An additional diluent or solvent may be added in the polymerization reactor by a separate feed port as aforementioned.

The above proposed configuration in FIG. 1 is suitable to operate at various paraffin conversions of the catalytic permreactor. However, high paraffin conversions and yields to olefin products are desirable in order to increase the production efficiency of the overall process per pass of paraffin feed (i.e., kg of polyolefin produced/kmol of paraffin feed). Thus, higher dehydrogenation temperatures and low pressures are necessary conditions in the permreactor to increase paraffin conversion and olefin yield. However, at reaction temperatures higher than about 600° C. usually the selectivity to the primary olefin decreases to less than 80%, with secondary olefins and possibly methane byproducts to be formed as well from side reactions. Therefore, selection of highly selective catalysts to the primary olefin is required to obtain high yields at higher temperatures. Also, an increase in the residence time of the paraffin in the permreactor causes an increase in the yield to the corresponding olefin at the expense of a reduced throughput from the reactor. Lower reaction pressures also increase the olefin yield.

FIG. 2 is an embodiment of a metal permreactor which replaces the inorganic or composite (metal-inorganic) one described in FIG. 1. This type of permreactor ensures removal of only hydrogen out of the dehydrogenation zone. Various hydrogen permselective metals and alloys can be utilized as permreactor wall materials (i.e., Pd, V, Nb, Pd/Ag, Pd/Pt). The reject stream consists of only olefin and the unreacted paraffin with small quantities on non-permeate hydrogen depending on the overall hydrogen removal efficiency of the metal permreactor. The reject from the permreactor stream is therefore a suitable feed into the polymerization reactor for production of high molecular weight polyolefins (e.g., polypropylene, polyethylene, polystyrene) which usually are linear and highly crystalline materials, due to the absence of hydrogen as chain transfer agent.

Similarly with the previous process described in FIG. 1, the metal permreactor is combined with a separator which separates olefin from paraffin and recycles the paraffin into the metal permreactor and the olefin into the polymerization reactor. A bypass valve in hydrogen permeate stream can ultimately allow metered amounts of hydrogen into the polymerization reactor feed, to control the polymer molecular weight.

The above described processes shown in FIGS. 1&2 can work as well for production of block and random copolymers of the type olefin 1-olefin 2 (i.e., primary olefin-secondary olefin). These products can be produced when the described dehydrogenation permreactors in FIGS. 1 and 2 operate at higher reaction temperatures (i.e., above 550–600° C.) and produce mixtures of primary and secondary olefins. As example, in the dehydrogenation of propane the exit stream contains mainly propylene with smaller quantities of ethylene. This olefinic product mixture after cooling, is suitable for the production of propylene-ethylene copolymers in the consecutive polymerization reactor which can operate either as a stirred bed or as a fluid bed.

In another feed modification, mixtures of propane and ethane can be fed in permreactor A for simultaneous dehydrogenation into a propylene-ethylene mixture for the subsequent production of block or random copolymers in the polymerization reactors D or C.

Thus, the variation of the permreactor type, wall material, and reaction conditions as well as the composition, flowrate and operating conditions of the inlet-feed stream into the permreactor affect the flowrate, composition and operating conditions of the exit olefinic stream which in series affects (controls) the polymerization process in the consecutive reactor.

Permreactor A in FIG. 1 and FIG. 2 can be replaced by a conventional fixed bed catalytic dehydrogenator for production of olefin-hydrogen-paraffin mixtures for feed in the consecutive polyolefin reactor. The olefin yield at the exit of such a dehydrogenator reactor will be usually lower than the one which corresponds to the membrane reactor due to the lack of the equilibrium shift effect in the yield. The process can be also used for dehydrogenation of other hydrocarbons such as ethylbenzene and butenes to the corresponding monomers and then to subsequent polymers.

Permreactor A in FIG. 1 and FIG. 2 can be also replaced by a paraffin (i.e., ethane, propane, butane) cracker which is a conventional (non-permeable) non-catalytic reactor to yield olefins (i.e., ethylene, propylene, butylene) and hydrogen which are used for the downstream polymerization into polyolefins. The cracker uses only thermal based dehydrogenation of paraffins to olefins without use of a catalyst. The reactor can be of plug flow type, vertical or horizontal. The process can be used also for dehydrogenation of other hydrocarbons such as ethylbenzene and butenes to the corresponding monomers and subsequent polymers.

Moreover, the polymerization reactors shown in FIG. 1 and FIG. 2, can be replaced by other type of synthesis reactors in the downstream of the membrane reactor for production of specialty chemicals such as oxygenated compounds. As an example, the produced ethylene from the ethane dehydrogenation membrane reactor can be used in the next reactor for the production of ethylene oxide, which alternatively, can be subsequently used for the production of ethylene glycol. The ethylene oxide production requires feed of oxygen or air together with ethylene in a catalytic type reactor. Ethylene oxide can be then converted to ethylene glycol in a slurry liquid phase type reactor. Moreover, ethylene with oxygen or air can be directly converted to acetaldehyde in a slurry liquid phase type reactor. Similar process can take place for propylene oxide production from a different reaction route as shown in the claims below.

Further, propylene from the propane dehydrogenation membrane reactor shown in FIG. 1 and FIG. 2 can be mixed with oxygen or air for subsequent production of acrolein or acrylic acid in a consecutive catalytic reactor. In a similar flow scheme the propylene can be mixed with oxygen or air, and ammonia in a consecutive catalytic reactor for production of acrylonitrile.

In addition to the described processes in FIGS. 1 and 2, the current invention disclosure describes integrated olefin-pamffln separators with fluid bed polymerization reactors into one operating module. Also, integrated dehydrogenation perinreactors with fluid bed polymerization reactors are described which produce polyolefins from paraffins within a single module.

The olefin-paraffin separators shown in embodiment of FIG. 3, can be fed with paraffins from various sources including refinery, postrefinery and petrochemical hydrocarbon mixtures. The integrated separator-polymerization reactor works in a tube and shell configuration. The feed mixture can be fed in the tube inlet where the separation of olefin from the paraffin occurs via the reactive walls of the tubular separator. The rejected paraffin exits via the tube outletand can be used in subsequent operations such as dehydrogenation, reforming or as a combustion fuel. The walls of the separator can be a reactive membrane which is made by a polymer, polymer-metal, polymertceramic, polymer-ceramic-metal, ceramic-metal, liquid like polymer, or other composite material containing reactive metals, wherein metals such as Cu. Ag, Zn, Cr, Mn, Fe, Ni, Co, Sn, Rh, Ru, Pd which have an affinity to form a transporting complex with the permeating olefin can be used in order to facilitate the transport of the olefin in the permeate side versus rejection of the paraffin. The permeate olefin in the shell of the separator is fluidized under inert gas flow and catalyst flow and is polymerized into the respective polyolefin. The tube and shell temperatures are similar because the two operations occur at relatively low temperatures, i.e., 50–200° C. Similarly the pressure in the two sides can be adjusted between 1–30 atmn to promote both operations, i.e., olefin separation and polymerization. The polyolefin product precipitates from the bottom of the polymerization reactor side. The unreacted olefin (monomer) from the polymerization with possible traces of permeated paraffin is recycled into the bottom of the reactor through a separate inlet for continuous polymerization. The process is suitable for the separation of ethylene-ethane, propylene-propane, butylene-butane, and higher olefin-paraffin hydrocarbons fed within the separator in the gaseous phase or vaporized in the separator inlet. Respectively, products such as polyethylene, polypropylene, polybutane-1 and higher polyolefins can be produced in the shell of the module. The process can be also adjusted to separate more than one olefins from paraffins. As an example, ethylene and propylene together can be separated via the membrane from the corresponding paraffins, and the olefinic mixture can be used for production of block and random copolymers in the polymerization reaction step.

The described process can be also flow reversed, with the hydrocarbon (paraffin) feed to enter into the shell and the polymerization to occur into the tube of the integrated module.

Another related invented process, pertains to the use of the described tube and shell membrane reactor configuration as a combined dehydrogenation and polymeization reactor. This embodiment is shown in FIG. 4. Accordingly, a paraffin such as ethane, propane, n-butane, i-butane or higher is fed in the tube of the two-reactor integrated module, which is filled with proper dehydrogenation catalyst for conversion of the paraffin to olefin. Such catalyst can be Pt, Ru, Rh, Cr, Ni or other related metals. The products olefin and hydrogen are separated through the high temperature membrane and are transferred in the shell of the reactor. The membrane which is used as a separation medium can be made by a ceramic, ceramic-metal, polymer, polymer-metal, polymer-ceramic, polymereramic-metal, metal, metal composite, or other composite material, which contains metals such as Cu, Ag, Zn, Cr, Mn, Sn, Fe, Ni, Co, Rh, Ru which make for a membrane with high separation affinity for the olefin and hydrogen and for rejection of the paraffin. The separation is based on the formation of a complex with the olefin and/or the hydrogen to enhance the permeation. The rejected paraffin exits from the outlet of the membrane reactor and is recycled into the tube inlet for continuous dehydrogenation. Inert gases are used in polymerization side of the reactor to cool the permeate olefin and hydrogen down to the proper polymerization temperature. The temperature of the olefin-hydrogen stream is dropped progressively in the radial direction and at a further radial distance (i.e, close to the inner wall of the reactor shell) fluidization of polymerization catalyst mixed with the inert gas takes place and the polymerization occurs. Gases such as argon, nitrogen or other paraffins such as propane, butane can be used as inert and cooling gases. The non-polymerized olefins are recycled into the bottom of the reactor shell for continuous polymerization, after passing through external coolers for cooling the gas and removing the heat of polymerization The solid polyolefins precipitate and exit through the bottom of the integrated reactor shell. In case in which significant quantities of paraffin permeate also through the membrane, an external separator is used to separate the non-polymerized olefin from the paraffin used as inert or diluent in polymerization, and to recycle the olefin into the polymerization reactor inlet for continuous polymerization. In case in which the dehydrogenation product is more than one olefins, block or random copolymers can be produced in the integrated polymerization zone. The process produces polymers of lower molecular weight due to the presence of hydrogen which is a chain transfer agent The described sequence of flow operations can be reversed, with the paraffin to be fed into the shell side inlet wherein dehydrogenation occurs and with the fluid bed polymerization reaction to take place in the tube side of the integrated dehydrogenation-polymerization reactor.

The described integrated process is suitable for production of polyethylene, polypropylene, polybutane-1, polyisobutylene, and higher polyolefins from the respective dehydrogenation of ethane, propane, n-butane, ibutane and higher paraffins.

DETAILED DESCRIPTION OF THE DRAWINGS

Figure 1:
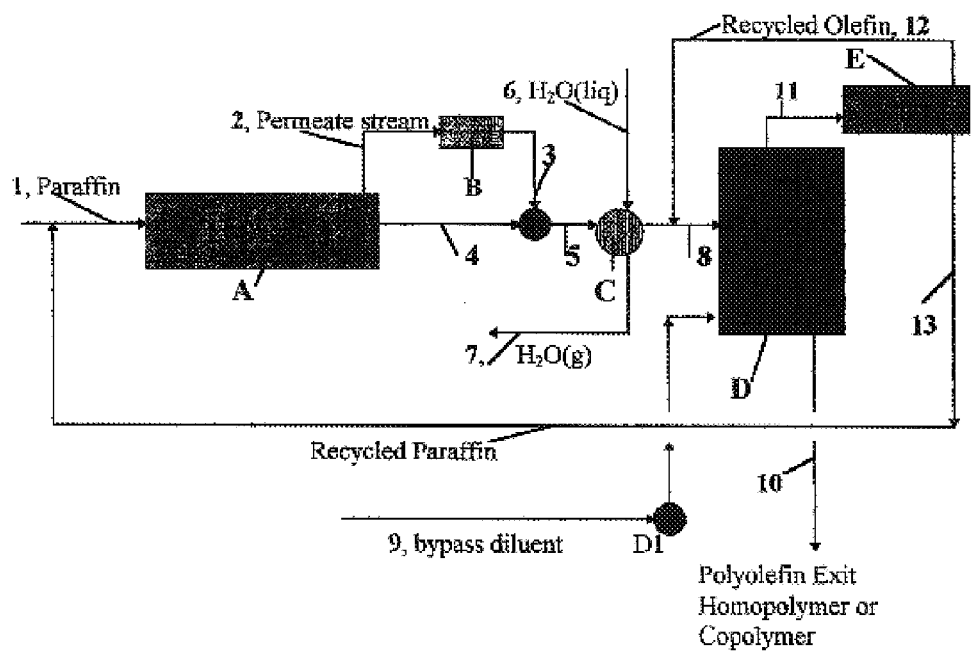

FIG. 1 depicts a membrane reactor (permreactor) which provides olefinic mixtures to the next polymerization reactor. The porous walls (e.g., inorganic) of the permreactor can be catalytic or inert and let one or more reactive species to permeate through in the shellside. The packed bed in tube-side can be filled with catalyst particles suitable for the dehydrogenation reaction such as Pt, Cr, Ru, Rh, Pt and other metals. The reject (feedside) and permeate (shellside) streams can be combined in the downstream of the permreactor and after proper cooling (heat exchanging) in the temperature of the polymerization reactor can be fed as a mixture into the inlet of the polymerization reactor.

Stream 1 in FIG. 1 is a paraffin such as ethane, propane, n-butane, i-butane or a mixture of paraffins or other hydrocarbons undergoing dehydrogenation. Stream 2 is the permeate stream from the reactor containing mainly hydrogen, olefin and smaller amounts of permeated paraffin. Stream 2 is compressed in compressor B and becomes stream 3 which has the same pressure with the reject stream 4. The two streams merge into a single stream 5 which is cooled in cooler (heat exchanger) C at the temperature of the polymerization reactor D and becomes the feed stream 8. Stream 9 is a bypass stream entering into reactor D from a different port, which contains a suitable additional solvent or diluent for the polymerization reaction such as hexane, heptane, isopentane. Valve D1 adjusts the flowrate of feed stream 9 in metered amounts. Stream 10 from the polymerization reactor D contains the produced polyolefin, while stream 11 contains a mixture of paraffins and unreacted olefins which are separated in permeator (membrane separator) E and are recycled respectively via streams 12 and 13 into the corresponding reactors.

Figure 2:
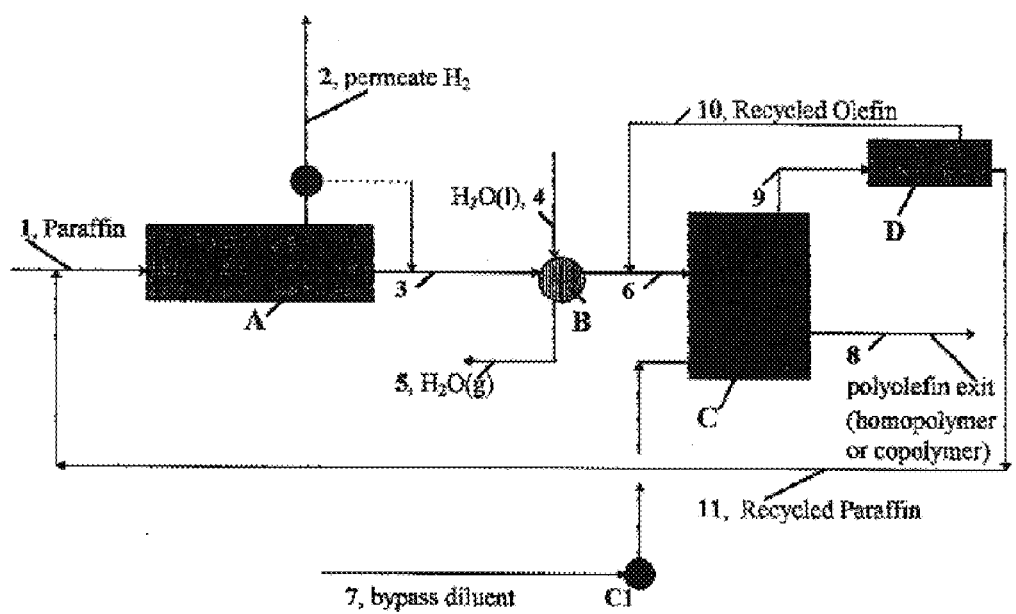

FIG. 2 depicts a dense (e.g., metal) permreactor which replaces the porous one described in FIG. 1. This type of permreactor wall material ensures removal of hydrogen only out of the dehydrogenation zone. Stream 1 in FIG. 2 is again a pain such as ethane, propane, n-butane, i-butane or a mixture of paraffins or other hydrocarbons undergoing dehydrogenation. Stream 2 is the permeate stream from the dense permreactor containing only hydrogen. Stream 3 is the reject (non-permeate) exit stream from the permreactor A containing olefins and unreacted paraffins which is cooled in cooler B at the temperature of the polymerization reactor C. Stream 6 enters into the polymerization reactor C. Stream 7 is a bypass stream entering into reactor C from a different port, which contains a suitable additional solvent or diluent for the polymerization reaction such as hexane, heptane, isopentane. Valve C1 adjusts the flowrate of feed stream 7 in metered amounts. Strean 8 exiting from reactor C contains the produced polyolefin, while stream 9 contains an exit mixture of paraffins and unreacted olefins which are separated in permeator-separator D and are recycled respectively to the corresponding vessels via streams 10 and 11.

Figure 3:
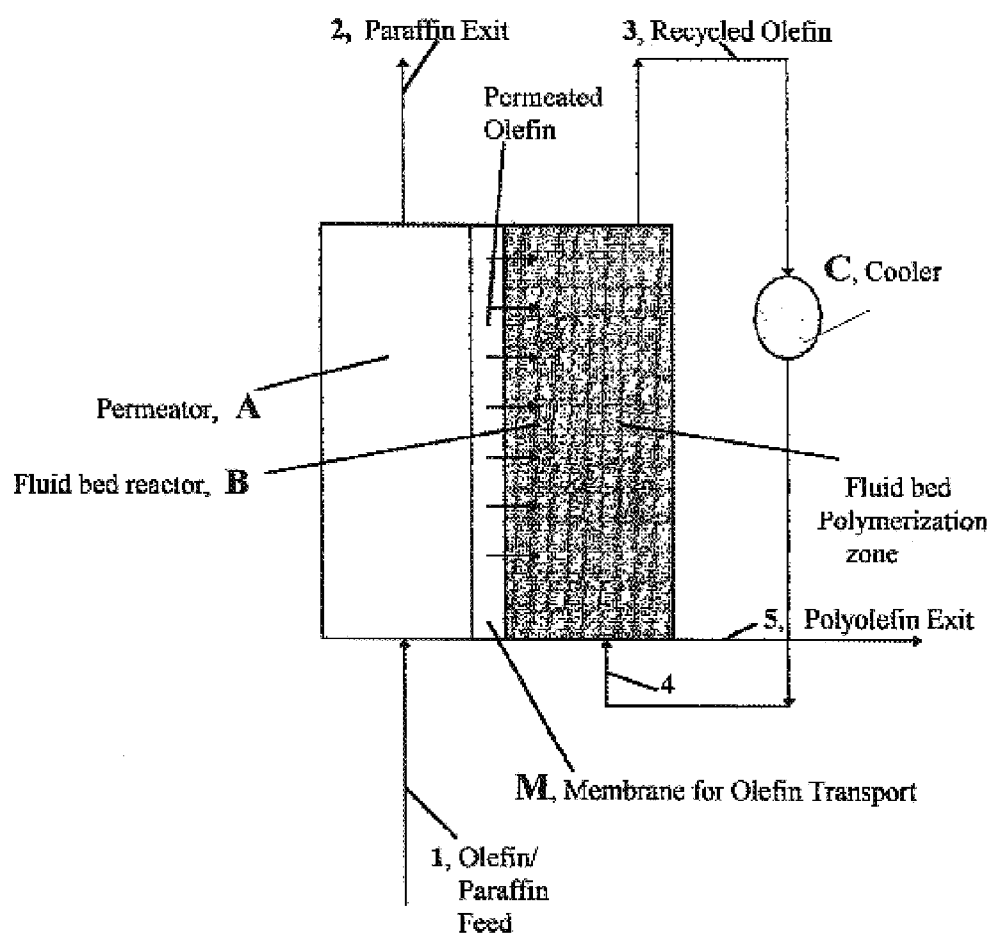

FIG. 3 depicts an integrated olefin-paraffin membrane separator with a fluid bed polymerization reactor for production of polyolefins. Stream 1 contains the olefin/paraffin feed mixture separated by the olefin selective membrane M; stream 2 is the rejected (non-permeated) by the membrane paraffin exiting from the membrane separator A Stream 3 is the unreacted recycled olefin from the polymerization zone B, which after proper cooling in cooler C becomes stream 4 entering back into polymerization reactor B. Gas phase-fluid bed type polymerization with suitable catalyst powder occurs in zone B. Stream 5 is the exit polymerized material.

Figure 4:
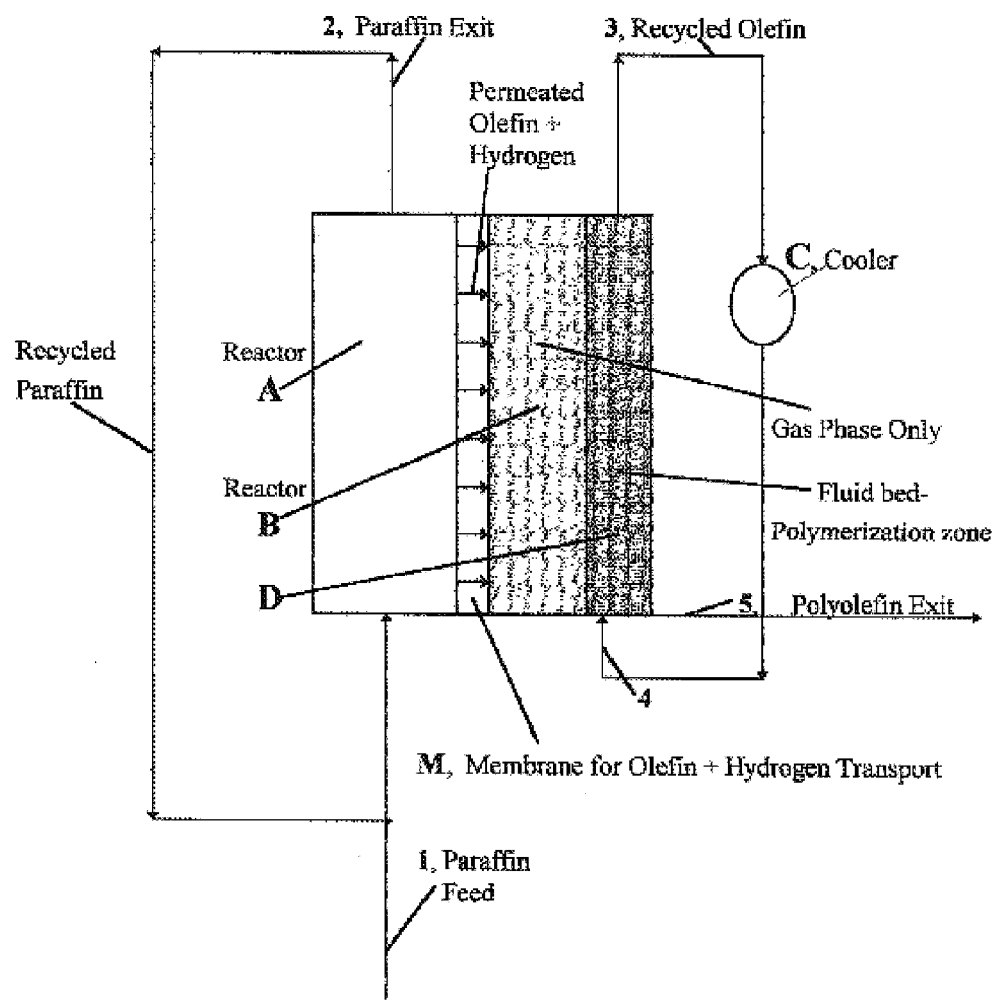

FIG. 4 depicts an integrated paraffin dehydrogenation membrane reactor with a fluid bed polymerization reactor for direct production of polyolefins and other polymers. Stream 1 is the paraffin feed, which is catalytically dehydrogenated in reactor A, and mainly the olefin and hydrogen products are transported through the selective membrane M. Stream 2 is the unreacted recycled paraffin going back into the membrane reactor A. Zone B in the shell of the integrated module is for gas flow only to cool the permeate olefin and hydrogen in the polymerization temperature and no reaction occurs in zone B. Polymerization reaction occurs in fluid bed zone D of the integrated module wherein also fluidized flow of suitable catalyst powder takes place. Stream 3 is the unreacted recycled olefin into the polymerization zone D, which after cooling in cooler C becomes stream 4 entering back into the reaction zone D. Stream 5 is the exit polymerized material.

Figure 5:
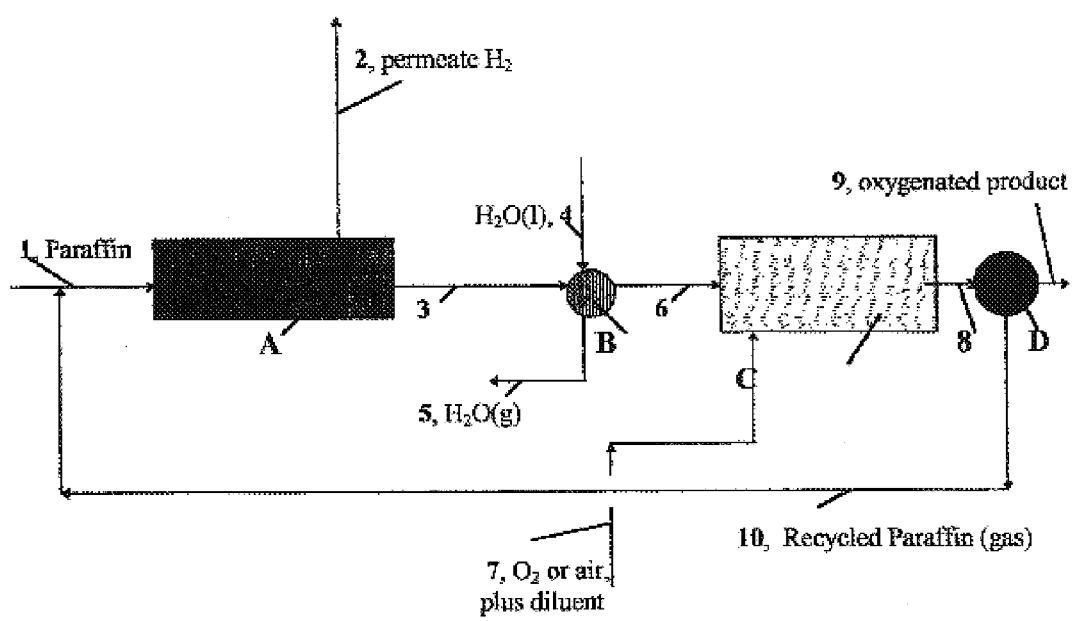
FIG. 5, is an embodiment which relates to this of FIG. 2. But the consecutive polymerization reactor is replaced with a synthesis reactor for production of oxygenated compounds or specialty chemicals.

FIG. 5 depicts a permreactor which is made preferably by dense materials (e g, metal or dense inorganics) rather than porous materials. This type of pernreactor wall materials ensures removal of hydrogen only out of the dehydrogenation zone. Stream 1 in FIG. 5 is again a paraffin such as ethane, propane, n-butane, i-butane or a mixture of paraffins. Stream 2 is the permeate stream from the dense permreactor containing only hydrogen. Stream 3 is the reject (non-permeate) exit stream from the pemireactor A containing olefins and traces of unreacted paraffins which is cooled in cooler B at the temperature of the downstream synthesis reactor C. Stream 6 enters into the synthesis reactor C together with bypass stream 7 which provides air or oxygen with a diluent if necessary, into the same reactor C. The synthesis reaction is usually also catalytic and a suitable bed of catalyst exists within the reactor C. Usually this type of process configuration is suitable for production of oxygenated compounds from olefins such as ethylene oxide, acetaldehyde, acrolein, acrylic acide, acrylonitrile. Stream 8 is the exit product stream, specialty chemical such as an oxygenated compound from reactor C mixed with traces of unreacted paraffins and olefins. Stream 8 passes through an absorber, water scrubber or a cryogenic trap D which separates readily the oxygenated compounds (products) in liquid phase or dissolved into water, as stream 9, while the rest of hydrocarbons exit from a different exit in gas phase as stream 10 which is recycled back into the inlet stream 1.

Figure 6:
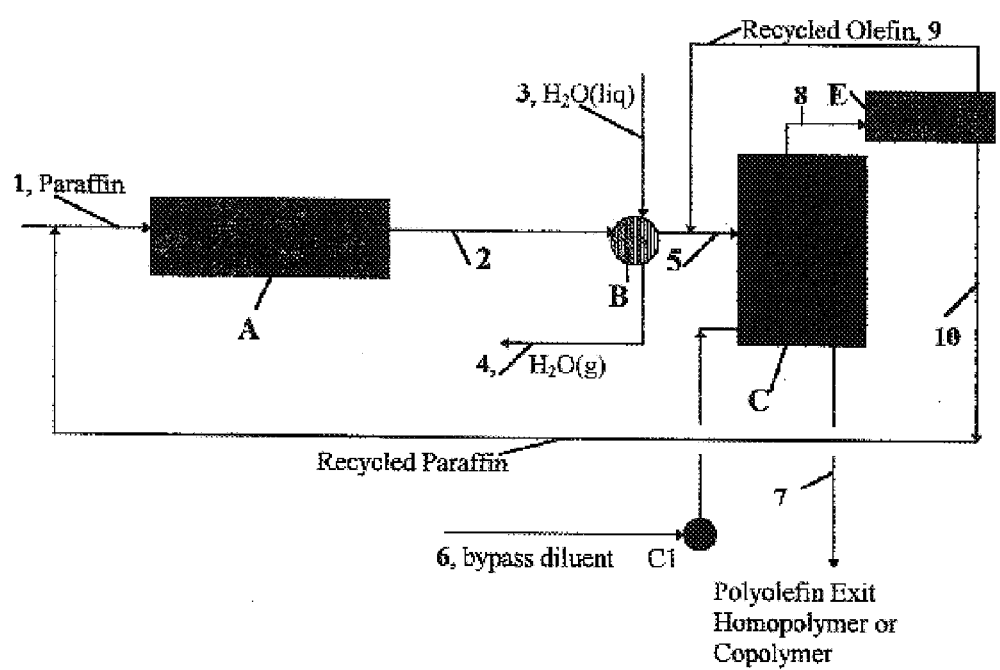
FIG. 6, is an embodiment which relates to this of FIG. 1. But the firt membrane reactor for dehydrogenation is replaced by a non-permeable catalytic or non-catalytic reactor which has a single outlet from which all products and unconsumed reactants exit

FIG. 6 depicts a conventional (non-permeable) plug flow type catalytic reactor or a non-catalytic cracker which are replacing the membrane reactor (permreactor) shown in FIGS. 1&2. Stream 1 in FIG. 6 is a paraffin such as ethane, propane, n-butane, i-butane or a mixture of paraffins or a higher hydrocarbon such as ethylbenzene. Stream 2 is the only product exit stream from permreactor A containing olefins or other monomers, unreacted paffins (or other reactants) and hydrogen. Stream 2 is cooled in cooler B at the temperature of the next polymerization reactor C. Stream 5 enters into the polymerization reactor C. Stream 6 is a bypass stream entering into reactor C from a different port, which contains a suitable additional solvent or diluent for the polymerization reaction in C, such as hexane, heptane, isopentane. Valve D1 adjusts the flowrate of the feed stream 6 in metered amounts. Stream 7 exiting from reactor C contains the produced polyolefin or other polymer, while stream 8 contains a mixture of paraffins (or other reactants) and unreacted olefins (or other monomers) which are separated in permeator-separator D and are recycled respectively into the corresponding vessels via streams 9 (goes back into reactor C) and 10 (it is recycled into initial reactor A).

REFERENCES CITED

1. Vasileiadis, S., Ziaka, Z., "Polymer grade olefin production with multifunctional permreactor-permeator systems"; NASCRE 1st, Houston, Tex. January 2001.
2. Ser van der Ven, (1990). "Polypropylene and other Polyolefins, Polymerization and Characterization", Studies in Polymer Science 7, Elsevier Sci.
3. Moore, E. P. Jr., (1998). "The Rebirth of Polypropylene-:Supported Catalysts", Hanser Publishers.
4. Rodriguez F., (1989). "Principles of Polymer Systems", Hemisphere Publ. Corp., $3^{rd}$ Ed.
5. F. W. Billmeyer, (1984). "Textbook of Polymer Science", J. Wiley & Sons, $3^{rd}$ Ed.
6. Vasileiadis, S., Ziaka, Z., (2000), "Environmentally benign hydrocarbon processing applications of single and integrated permreactors", in Reaction Engineering for Pollution Prevention, Elsevier Sci., pp. 247–304.
7. Ziaka, Z., (1994), "Experimental and modeling studies of the catalytic propane dehydrogenation reaction in ceramic membrane reactors", Ph.D. dissertation, University of Southern California, Los Angeles, Calif.
8. Kim Y. H., Ryu J. H., Bae J. Y., Kang Y. S. and Kim H. S. (2000). "Reactive Polymer Membranes Containing Cuprous Complexes in Olefin/Paraffin Separation", *Chem. Commun.*, (Comm.#a908395b) pp. 195–196.
9. Vasileiadis, S., Ziaka, Z., (1999). Alternative generation of $H_2$, CO and $H_2$, $CO_2$ mixtures from steamcarbon dioxide reforming of methane and the water gas shift with permeable (membrane) reactors. *Chem Eng. Comm.*, 176, 247.
10. Ziaka, Z., Vasileiadis, S., (1997). "Polymer Membrane Reactors for Enhanced Hydrocarbon Conversion and Upgrading", *AIChE Annual meeting*, paper #275c.

We claim:

1. A process which catalytically dehydrogenates paraffin hydrocarbon feedstocks over a bed of metallic catalyst in a membrane based dehydrogenation reactor to produce olefins and hydrogen, with the permeate stream from the membrane reactor to consist mainly of hydrogen, olefin, and lesser amounts of permeated paraffin, with the non-permeate stream from the membrane reactor to consist of olefin, hydrogen and unreacted paraffin, with the membrane in the dehydrogenation reactor to be an inorganic membrane, inorganic-metal membrane, or metal based membrane made by one or more of the following ceramic oxides:

alumina ($Al_2O_3$), titania ($TiO_2$), silica ($SiO_2$), zirconia ($ZrO_2$), mixed with one or more of the following catalytic metals:
Pt (platinum), Cr (chromium), Pd (palladium), Cu (copper), Zn (zinc), V (vanadium), Mg (magnesium), Ru (ruthenium), Rh (rhodium), Ni (nickel), Fe (iron), Sn (tin), Mo (molybdenum), or with the membrane to be made by the following metal and metal alloys:
Palladium,
Palladium-Silver,
Palladium-Platinum,
Palladium-Platinum-Silver,
Vanadium,
Palladium-Vanadium,
Palladium-Vanadium-Silver,
Niobium,
Palladium-Niobium,
Palladium-Niobium-Silver,
Tantalum,
Palladium-Tantalum,
Palladium-Tantalum-Silver,
Zirconium,
Palladium-Zirconium,
Palladium-Zirconium-Silver, with the permeate and non-permeate streams to merge in the downstream of the membrane reactor by re-compressing the permeate stream into the same pressure with the non-permeate stream, with the merged stream to pass through a heat exchanger to reduce its temperaturte by exchanging heat and generating steam, with the cooled mixture stream to be fed into a polymerization reactor for polymerization reaction to a polyolefin, after mixing with a bypass-fed solvent in vapor, gas, or liquid phase, with the polymerization reactor to be of gas-phase, fluid bed type of of slurry-solution phase, stirred bed type, with the formed polymer to exit from the polymerization reactor in the form of particles, granules or foam, with the hydrogen produced from the dehydrogenation reaction to be used in the polymerization reactor as a chain transfer agent to regulate and reduce the polymer molecular weight, with the unreacted paraffin from the dehydrogenation reactor to be used in the polymerization reactor as a diluent, solvent or heat removing medium, with the unreacted olefin and paraffin from the polymerization to exit from the top of the polymerization reactor and enter into a membrane separator which separates the olefin from the paraffin and recycles the olefin into the inlet of the polymerization reactor and the paraffin into the inlet of the initial membrane dehydrogenation reactor, with the membrane in the downstream membrane separator to be a dense, porous, or liquid like synthetic polymer or composite type membrane containing one or more of the following metal ions, Cu (copper), Ag (silver), Cr (chromium), Fe (iron), Zn (zinc), Sn (tin), Co (cobalt), Ni (nickel), Mn (manganese), V (vanadium), Ti (titanium), Ru (ruthenium), Rh (rhodium), and with the polymer material of the membrane to consist by one or more of the following: poly(methyl methacrylate), poly(methyl acrylate), polystyrene, poly(vinyl acetate), poly(vinyl pyrrolidone), poly(vinyl carbazole), poly(vinyl stearate), poly (β-propiolactone), polydiketene, polytrioxane, poly(acrylic ester), polyacrylonitrile, polymethacrylonitrile, poly(acrylic acid), poly (methacrylic acid), poly(vinyl chloride), poly (vinylidene chloride), polytetrafluoroethylene, polychlorotrifluoroethylene, poly(vinyl fluoride), poly (vinylidene fluoride), polyimides, polycarbonates, polysulfones, polybenziimidazoles, polyphosphazenes, polyamides, polycaprolactams, parylenes, polysiloxanes.

2. The process of claim 1 wherein the initial feedstock is either ethane or propane and the dehydrogenation reaction of ethane to ethylene or of propane to propylene is occurring respectively in the catalytic membrane dehydrogenation reactor, and the conversion of ethylene to polyethylene or of propylene to polypropylene is occurring in the next polymerization reactor with polyethylene or polypropylene respectively to be the final polymer product.

3. The process of claim 1 wherein the initial feedstock is either n-butane or i-butane or 4-methylpentane, and the dehydrogenation reaction of n-butane to butene-1, or of i-butane to isobutene, or of 4-methylpentane to 4-methylpentene-1, is occurring in the membrane catalytic dehydrogenation reactor and the conversion of butene-1 to poly(butene-1), or of isobutane to poly(isobutene), or of 4methylpentene-1 to poly(4-methylpentene-1), is occurring in the next polymerization reactor with poly(butene-1) or poly(isobutene) or poly(4-methylpentene-1) to be the final polymer product.

4. The process of claim 1 wherein the initial feedstock is ethylbenzene and the dehydrogenation reaction of ethylbenzene to styrene is occurring in the membrane catalytic dehydrogenation reactor and the conversion of styrene to poly(styrene) is occurring in the next polymerization reactor with poly(styrene) to be the final polymer product.

5. The process of claim 1 wherein the initial feedstock is either butene-1 or butene-2 or a mixture of both alkenes, and the dehydrogenation reaction of butene-1 to 1,3-butadiene or of butene-2 to 1,3-butadiene or both of these reactions are occurring in the membrane catalytic dehydrogenation reactor and the conversion of 1,3-butadiene to poly(1,3-butadiene) is occurring in the next polymerization reactor with poly(1,3-butadiene) to be the final polymer product.

6. The process of claim 1 wherein the feedstock in the initial dehydrogenation reactor is one of the following:

propane for final production of propylene-ethylene copolymers, ethane, propane mixture for final production of ethylene-propylene copolymers, n-butane or i-butane for final production of butylene-propylene-ethylene copolymers, or butylene-propylene copolymers, or butylene-ethylene copolymers, another paraffin, or another saturated or unsaturated hydrocarbon, or naphtha, for dehydrogenation and final polymerization of the dehydrogenated compounds into the corresponding polymers.

7. The process of claim 1 wherein the initial membrane dehydrogenation reactor is a non-catalytic thermal cracker, with all products and unreacted reactants to exit from the single outlet and directed after cooling into the polymerization reactor for production of the corresponding polyolefins.

8. The process of claim 7 wherein the feedstock in the initial membrane dehydrogenation thermal cracker is one of the following:
- ethane, for final production of polyethylene,
- propane, for final production of polypropylene,
- ethane, propane mixture for final production of ethylene-propylene copolymers,
- n-butane, for final production of poly(butene-1),
- i-butane, for final production of poly(isobutene),
- n-butane or i-butane for final production of butylene-propylene-ethylene copolymers, or butylene-propylene copolyers, or butylene-ethylene copolymers,
- 4-methylpentane-1 for final production of poly(4-methylpentene-1),
- ethylbenzene for final production of poly(styrene),
- butene-1 for final production of 1,3-butadiene,
- butene-2 for final production of 1,3-butadiene,
- butene-1 and butene-2 mixture, for final production of 1,3-butadiene,
- another paraffin, or another saturated or unsaturated hydrocarbon, or naphtha, for dehydrogenation and final polymerization of the dehydrogenated compounds into the corresponding polymers.

9. The process of claim 1 wherein the metal or metal alloy membrane allows only hydrogen to permeate through into the permeate stream, and the non-permeate stream contains no hydrogen or only small amounts of non-permeated hydrogen mixed with the olefin product and the unreacted paraffin, and with the final polyolefin product from the polymerization reactor to be of high molecular weight due to the absence of the hydrogen chain transfer effect during the polymerization.

10. The process of claim 9 wherein the feedstock in the initial metal membrane dehydrogenation reactor is one of the following components:
- ethane, for final production of polyethylene,
- propane, for final production of polypropylene,
- ethane, propane mixture for final production of ethylene-propylene copolymers,
- n-butane, for final production of poly(butene-1),
- i-butane, for final production of poly(isobutene),
- n-butane or i-butane for final production of butylene-propylene-ethylene copolymers, or butylene-propylene copolyers, or butylene-ethylene copolymers,
- 4-methylpentane-1 for final production of poly(4-methylpentene-1),
- ethylbenzene for final production of poly(styrene),
- butene-1 for final production of 1,3-butadiene,
- butene-2 for final production of 1,3-butadiene,
- butene-1 and butene-2 mixture, for final production of 1,3-butadiene,
- another paraffin, or another saturated or unsaturated hydrocarbon, or naphtha, for dehydrogenation and final polymerization of the dehydrogenated compounds into the corresponding polymers.

11. A process which integrates a membrane separator and a polymerization reactor into a single module, with the feed in the separator to consist of an olefin-paraffin mixture, with the olefin to be separated from the paraffin by the use of a membrane in the membrane separator, with the membrane to be a dense, porous or liquid like synthetic polymer or composite membrane containing one or more of the following metal ions: Cu (copper), Ag (silver), Cr (chromium), Fe (iron), Zn (zinc), Tin (Sn), Co (cobalt), Ni (nickel), Mn (manganese), V (vanadium), Ti (titanium), Ru (ruthenium), Rh (rhodium), with the flow mode in the membrane separator to be of plug flow, mixed (stirred) flow or fluid bed flow type, with the non-permeate paraffin to exit as non-permeate stream from the separator exit, with the permeate through the membrane olefin to undergo fluidization without or with stirring with gas phase polymerization to occur and conversion into polyolefin at the same time in the adjacent polymerization reactor by using suitable metallic catalyst in the form of fluidized powder or particles, with the unreacted olefin from the polymerization to exit from the top of the integrated polymerization reactor and after passing through a cooler to remove the exothermic heat of polymerization to be recycled back into the inlet of polymerization reactor for continuous polymerization, with the produced polyolefin product to exit from a separate exit in the form of particles, granules, or foam, and finally with the polymer material of the membrane in the integrated separator to consist by one or more of the following: poly(methyl methacrylate), poly(methyl acrylate), polystyrene, poly(vinyl acetate), poly(vinyl pyrrolidone), poly(vinyl carbazole), poly(vinyl stearate), poly($\beta$-propiolactone), polydiketene, polytrioxane, poly(acrylic ester), polyacrylonitrile, polymethacrylonitrile, poly(acrylic acid), poly(methacrylic acid), poly(vinyl chloride), poly(vinylidene chloride), polytetrafluoroethylene, polychlorotrifluoroethylene, poly(vinyl fluoride), poly(vinylidene fluoride), polyimides, polycarbonates, polysulfones, polybenziimidazoles, polyphosphazenes, polyamides, polycaprolactams, parylenes, polysiloxanes.

12. The process of claim 11 wherein the feedstock in the inlet of the integrated membrane separator-polymerization reactor is one of the following mixtures:
- ethane, ethylene mixture for final production of polyethylene,
- propane, propylene mixture for final production of polypropylene,
- ethane, propane, ethylene, propylene mixture for final production of ethylene-propylene copolymers,
- n-butane, butene-1 mixture for final production of poly(butene-1),
- i-butane, isobutene mixture for final production of poly(isobutene),
- 4-methylpentane-1, 4-methylpentene-1 mixture for final production of poly(4-methylpentene-1),
- mixtures of hydrocarbons with butenes, propylene, ethylene for final production of $C_2$–$C_4$ copolymers,
- another paraffin, olefin mixture or hydrocarbon, olefin mixture, or naphtha mixtures, for olefin separation via the membrane and final polymerization of the separated olefin into the corresponding polymer.

13. A process which integrates a membrane catalytic reactor and a polymerization reactor into a single module, with the feed in the membrane reactor to consist of a paraffin which is dehydrogenated into an olefin by the use of metallic catalyst, with the flow mode in the membrane reactor to be of plug flow, mixed (stirred) flow, or fluid bed flow type, with products olefin and hydrogen to be produced from the dehydrogenation reaction and permeate through the membrane into the adjacent polymerization reactor side, with the membrane to be of dense or porous structure or inorganic, inorganic-metal, inorganic-polymer or composite nature containing one or more of the following metal ions: Cu (copper), Ag (silver), Cr (chromium), Fe (iron), Zn (zinc), Sn (tin), Co (cobalt), Ni (nickel), Mn (manganese), V (vanadium), Ti (titanium), Ru (ruthenium), Rh (rhodium), with the non-permeate stream containing mainly unreacted paraffin and traces of olefin and hydrogen to exit as reject stream from the membrane reactor outlet and recycled back into the membrane reactor inlet for continuous dehydrogenation, with the permeate from the membrane olefin product to undergo fluidization without or with stirring and with gas phase polymerization conversion into polyolefin to occur in the adjacent integrated polymerization reaction module by using suitable metallic catalyst in the form of powder or particles, with the permeate hydrogen to be used in polymerization as a chain transfer agent to regulate and reduce the polymer molecular weight, with the unreacted olefin to exit from the top of the polymerization reactor and after passing through a cooler to remove the exothermic heat of polymerization, to be recycled back into the reactor for continuous polymerization, with the produced polyolefin product to exit from a separate exit in the form of particles, granules or foam, with the membrane in the integrated module to be made by one or more of the following ceramic oxides:
      alumina ($Al_2O_3$),
      titania ($TiO_2$),
      silica ($SiO_2$),
      zirconia ($ZrO_2$),
        mixed with one or more of the following catalytic metals: Pt (platinum), Cr (chromium), Pd (palladium), Cu (copper), Zn (zinc), V (vanadium), Mg (magnesium), Ru (ruthenium), Rh (rhodium), Ni (nickel), Fe (iron), Sn (tin), Mo (molybdenum),
      and possibly with one or more of the following polymer materials: poly(methyl methacrylate), poly(methyl acrylate), polystyrene, poly(vinyl acetate), poly (vinyl pyrrolidone), poly(vinyl carbazole), poly (vinyl steatate) poly(β-propiolactone), polydiketene, polytrioxane, poly(acrylic ester), polyacrylonitrile, polymethacrylonitrile, poly(acrylic acid), poly (methacrylic acid), poly(vinyl chloride), poly (vinylidene chloride), polytetrafluoroethylene, polychlorotrifluoroethylene, poly(vinyl fluoride), poly(vinylidene fluoride), polyimides, polycarbonates, polysulfones, polybenziimidazoles, polyphosphazenes, polyamides, polycaprolactams, parylenes, polysiloxanes.

14. The process of claim 13, wherein the feedstock in the inlet of the integrated membrane reactor-polymerization reactor module is one of the following:

ethane for final production of polyethylene,
    propane for final production of polypropylene,
    ethane, propane mixture for final production of ethylene-propylene copolymers,
    n-butane for final production of poly(butene-1),
    i-butane for final production of poly(isobutene),
    4-methylpentane-1 for final production of poly(4-methylpentene-1),
    ethylbenzene for final production of poly(styrene),
    butene-1 for final production of 1,3-butadiene,
    butene-2 for final production of 1,3-butadiene,
    butene-1, butene-2 for final production of 1,3-butadiene,
    mixtures of butanes, propane, ethane or naphtha for final production of $C_2$–$C_4$ copolymers,
    another paraffin or hydrocarbon feed for dehydrogenation into an olefin and final polymerization of the separated olefin into the corresponding polymers.

15. The process of claim 9 which relates with the ethane to ethylene dehydrogenation reaction and the production of ethylene, wherein oxygen or air with or without a diluent is added into the consecutive reactor and the consecutive reactor is replaced by a catalytic ethylene oxide-direct production reactor.

16. The process of claim 15 wherein the ethylene oxide product is fed into a next, downstream slurry-liquid phase reactor for production of ethylene glycol by hydration.

17. The process of claim 9 which relates with the ethane to ethylene dehydrogenation reaction and the production of ethylene, wherein oxygen or air with or without a diluent is added into the consecutive reactor and the consecutive reactor is replaced by a slurry-liquid phase catalytic reactor for direct production of acetaldehyde.

18. The process of claim 9 which relates with the propane to propylene dehydrogenation reaction and the production of propylene, wherein oxygen with or without steam, or air with or without steam are added into the consecutive reactor and the consecutive reactor is replaced by a catalytic reactor for the production of acrolein and acrylic acid.

19. The process of claim 9 which relates with the propane to propylene dehydrogenation reaction and the production of propylene, wherein oxygen and ammonia, or air and ammonia are added into the consecutive reactor and the consecutive reactor is replaced by a catalytic reactor for the production of acrylonitrile.

20. The process of claim 9 which relates with the propane to propylene dehydrogenation reaction and the production of propylene, wherein a hydroperoxide, or a mixture of ethylbenzene with air, or isobutane with air, are added into the consecutive reactor and the consecutive reactor is replaced by a catalytic reactor for the production of propylene oxide, with propylene oxide to optionally hydrated in a next downstream reactor for production of propylene glycol.

\* \* \* \* \*